(12) United States Patent
Phan

(10) Patent No.: US 7,021,463 B2  
(45) Date of Patent: Apr. 4, 2006

(54) PEN NEEDLE SHARPS PORT

(75) Inventor: Vu Phan, Edison, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 388 days.

(21) Appl. No.: 10/236,192

(22) Filed: Sep. 6, 2002

(65) Prior Publication Data

US 2005/0016883 A1    Jan. 27, 2005

(51) Int. Cl.
*B65D 85/24*    (2006.01)

(52) U.S. Cl. ........................... 206/366; 220/908

(58) Field of Classification Search ........ 206/364–366, 206/370, 63.5, 1.5, 210; 220/345, 346, 348, 220/254, 336, 326, 796–799, 908; 604/110, 604/192, 263, 197, 198; 222/153, 480, 516, 222/548, 553; 229/7 SC, 907; 215/231, 215/354; 53/468

See application file for complete search history.

(56) References Cited

U.S. PATENT DOCUMENTS

| | | | | |
|---|---|---|---|---|
| 4,667,821 A | * | 5/1987 | Shillington | 206/366 |
| 4,802,579 A | * | 2/1989 | Hall et al. | 206/366 |
| 4,875,265 A | * | 10/1989 | Yoshida | 29/240 |
| 5,092,462 A | * | 3/1992 | Sagstetter et al. | 206/366 |
| 5,249,680 A | * | 10/1993 | Shillington | 206/366 |
| 5,409,112 A | * | 4/1995 | Sagstetter | 206/366 |
| 5,474,181 A | * | 12/1995 | Shillington et al. | 206/370 |
| 6,036,671 A | * | 3/2000 | Frey | 604/110 |
| 6,062,001 A | * | 5/2000 | Kunik | 53/468 |
| 6,202,843 B1 | * | 3/2001 | Kelson et al. | 206/366 |
| 6,247,592 B1 | * | 6/2001 | Racicot et al. | 206/366 |
| 2004/0188295 A1 | * | 9/2004 | Hansen | 206/366 |

* cited by examiner

*Primary Examiner*—Mickey Yu  
*Assistant Examiner*—Jerrold Johnson  
(74) *Attorney, Agent, or Firm*—Alan W. Fiedler

(57) ABSTRACT

The present invention is a mechanical contrivance integrated into the closure of a sharps collector. It is intended to allow for the safe removal and disposal of a used pen needle from a pen syringe device. The pen syringe, with the used pen needle attached, is inserted into the specially designed port of the present invention. The pen syringe is then rotated counterclockwise about its longitudinal axis. The pen needle itself is constrained by at least one tooth, which only allows the pen needle one degree of freedom (linear displacement along its longitudinal axis). These conditions cause the pen needle to be unthreaded from the pen syringe, such that when the pen syringe is withdrawn from the port, a tang then blocks the pen needle from being withdrawn with the pen syringe, and the used pen needle falls into the sharps collector without the use of a secondary operation.

10 Claims, 4 Drawing Sheets

PEN NEEDLE SHARPS PORT

BACKGROUND

1. Field of the Invention

The present invention generally relates to containers for safely disposing used medical instruments and, more particularly, to a sharps disposal container adapted for disposing of pen syringe needles.

2. Description of Related Art

Disposal of standard medical sharps, such as surgical knives, blades, hypodermic needles and the like is a problem for hospitals and other healthcare facilities. Used sharps may become contaminated by body fluids and the like creating a hazard for anyone that may handle them following their use. Hospitals have developed stringent policy procedures for the safe disposal of used sharps, such as requiring sharps disposal containers in the emergency and examining rooms, and each patient room. Because of their potentially dangerous nature, particularly with present concerns regarding accidental transmittal of infectious diseases and syringe reuse, typical sharps disposal containers are designed not only to permit disposal but also to prevent unintentional contact with or theft of any object deposited in the disposal container.

The present growing trend of providing home healthcare tremendously increases the potential for inadvertent handling of used sharps, particularly of needles used in the home. Many patients must administer multiple doses of medication daily. Some home patients use syringes, and some use Pen syringes, while some patients use both. A pen syringe is particularly suitable for administering such multiple doses. An example of such pen syringes and pen syringe needles may be found is U.S. Pat. No. 6,146,361. Typically, pen needles are threadably engaged to pen syringes. The patient must therefore safely dispose many needles, especially pen syringe needles.

Openings to the sharps containers have been adapted with specific features to allow the removal of various standard sharps from a medical device and deposition within the container, however the design of pen syringe needles presents a problem, in that the diameter of a pen syringe needle is typically larger than the diameter of the standard hypodermic needle. There is a need therefore, for a container for disposing pen syringe needles, in which the container may be economically manufactured while providing an adequate level of safety to the user, and yet preventing unintentional exiting of sharps from within the container, and proved for easy removal of pen needles from the pen syringe, without allowing used needles to exit the container.

Medical care provided in the patient's home exposes not only the patient but also other individuals without medical experience to the inherent dangers of used needles. Existing sharps disposal containers typically include specially adapted orifices that permit sharps, such as needles, to be placed within the container, however a design that allowed removal of pen syringe needles has been lacking. Furthermore, removal of pen syringe sharps with a single hand would be desirable for a patient. Existing Sharps containers have openings to provide for access of the used sharps into the container, a majority of these openings are configured for removal of hypodermic syringe and blood access needles. What is needed is a container that has an opening suitable for removal of pen needles, utilizing a single hand. However, a simple opening, (for example a hole sized to allow entrance of a pen needle) to allow the removal of pen needles may allow used sharps to exit the container. Furthermore, what is needed is an opening designed to remove pen needles without allowing other sharps within the container to exit the container.

A simple opening that is sized for a pen needle, engages the pen needle, and allows unthreading of the pen needle from the pen syringe has the disadvantage that it requires a secondary operation to disengage the pen needle from the opening to allow it to fall into the sharps container. Prior art devices require the user to unthread the pen needle by inserting the pen injector into a port with a circular arrangement of multiple teeth, which fully encircle the pen needle. Once this is accomplished, the pen needle must be pushed through with a secondary component in a secondary operation. Before this occurs, there is risk of an accidental needlestick from the exposed proximal end of the pen needle. In addition, there is a possibility of this separate secondary component being lost or misplaced. In this event, the pen needle would be retained within with the port, with little remedy for pushing the pen needle through or pulling the pen needle out. In addition, the prior art devices may not be compatible with all pen syringes. Furthermore, what is needed is a design that requires only a single operation by the patient to allow the pen needle to enter the sharps container and eliminates any secondary operations.

SUMMARY

The present invention is a mechanical contrivance integrated into the closure of a sharps container. One object of the invention is to allow for the safe removal and disposal of a used pen needle from a pen syringe device with a single operation by the user. The pen syringe, with the used pen needle attached, is inserted into a specially adapted port. The pen syringe is then rotated counterclockwise about its longitudinal axis which disengages the pen needle from the pen syringe. The pen needle itself is constrained by at least one tooth, which only allows the pen needle one degree of freedom (linear displacement along its longitudinal axis). These conditions cause the pen needle to be unthreaded from the pen syringe. Upon complete unthreading of the pen needle, the pen syringe is withdrawn from the port. A small tang blocks the pen needle from being withdrawn with the pen syringe. When the pen syringe is completely withdrawn from the port, the used pen needle falls into the sharps container.

The present invention does not grip the pen needle hub in the same fashion as does prior art devices. The arrangement of the tooth and the port is such that full containment of the pen needle within the port is not achieved, and the pen needle is allowed to fall into the sharps container. In an alternate embodiment of the invention, the port uses a plurality of gripping teeth in an arcuate path that encompass a portion of a full circle. The axis of the arc of gripping teeth is arranged at an angle to the closure's top surface. This unique geometry allows the pen needle to simply fall away from the plurality gripping teeth after the pen needle is unthreaded. In addition, the present invention port is designed to be compatible with the most widely used pen syringes.

BRIEF DESCRIPTION OF THE DRAWINGS

These and other features, aspects, and advantages of the present invention will become better understood with regard to the following description, appended claims, and accompanying drawings where:

DETAILED DESCRIPTION OF THE DRAWINGS

Figure 1:
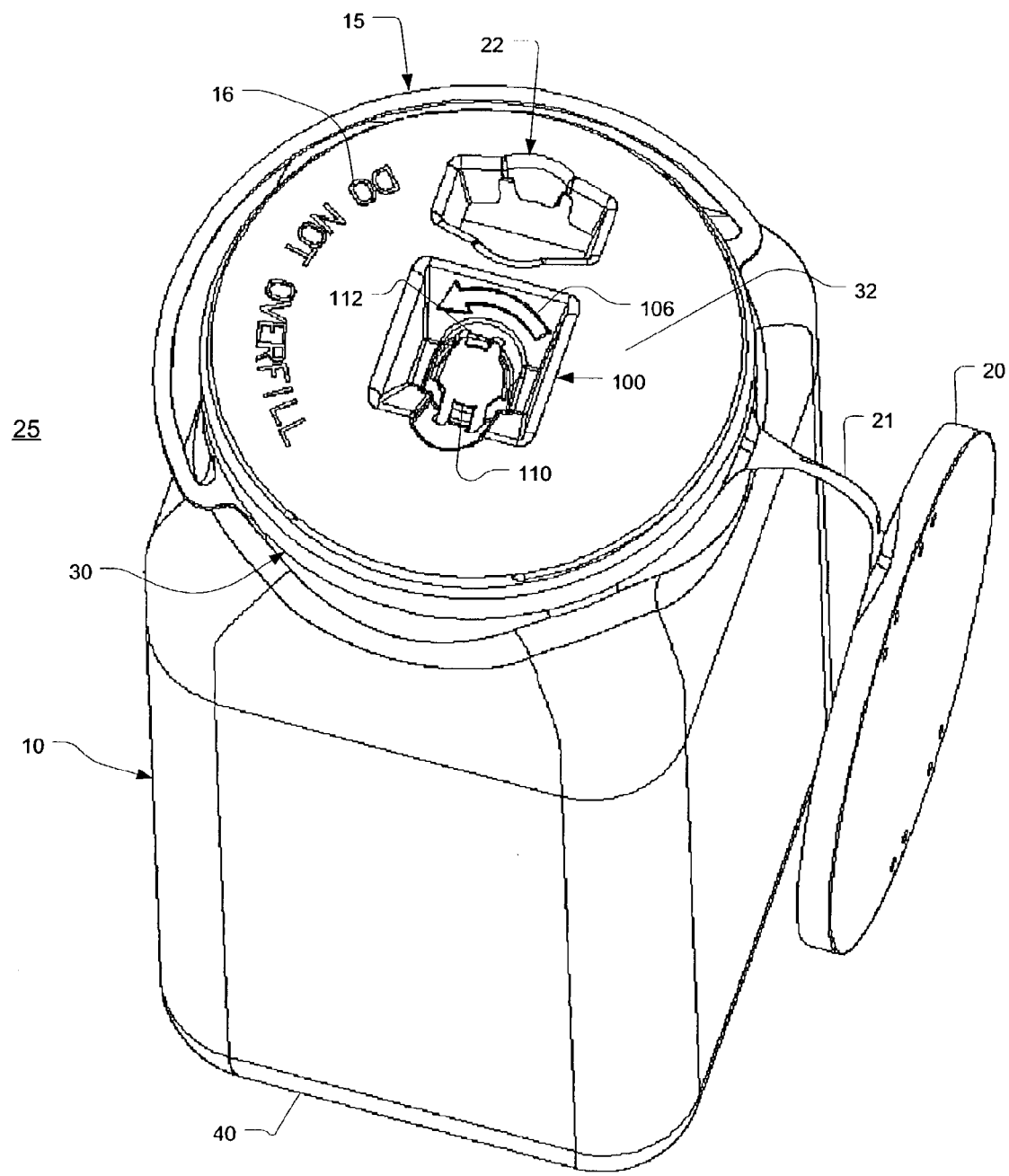
FIG. 1 illustrates a top perspective view of an exemplary sharps container having a port for removing pen needles according to the present invention.

FIG. 1 shows a sharps container 25, which contains pen needle port 100 of the present invention, herein referred to as port 100. Sharps container 25 is comprised of a closure 30 and a container 10. Container 10 is typically formed as a molded part with a plurality of sides and bottom 40. Closure 30 is typically attached to container 10 in a permanent fashion by a snap fit, however closure 30 may be welded or glued to container 10. Alternatively, closure 30 may be formed unitarily with container 10. Typically, all components are fabricated from molded plastic, although this is not critical to the operation of the present invention.

Closure 30 contains a handle 15 for easy carrying of sharps container 25. Attached to closure 30 is a lid 20 via a strap 21. In the case of the present invention, lid 20, strap 21 and closure 30 are formed unitarily via a single injection mold cavity. Alternatively, they could be separate components. Disposed on closure 30 may be indicia 16 to indicate usage instructions for sharps container 25. As shown in FIG. 1, indicia 16 is embossed text within the plastic of closure 30, which reads, "DO NOT OVERFILL." Also disposed on closure 30 is optional syringe opening 22. Syringe opening 22 is of a simple design that allows passage of hypodermic syringes into the interior of sharps container 25. Syringe opening 22 allows patients to dispose of syringes as well as pen needles into sharps container 25. Closure 30 has a top surface 32 and a bottom surface 34 (shown in FIG. 3).

Port 100, disposed on closure 30, may include directional indicia 106 which indicates to the user directions for use of port 100. Directional indicia as shown in FIG. 1 is an embossed portion of plastic in the form of a directional arrow to indicate to the user which way to turn a pen syringe for removal of a pen needle from a pen syringe. Port 100 is preferably integrally molded into closure 30, however port 100 could be molded as a separate part and assembled into an opening in closure 30.

Figure 2:
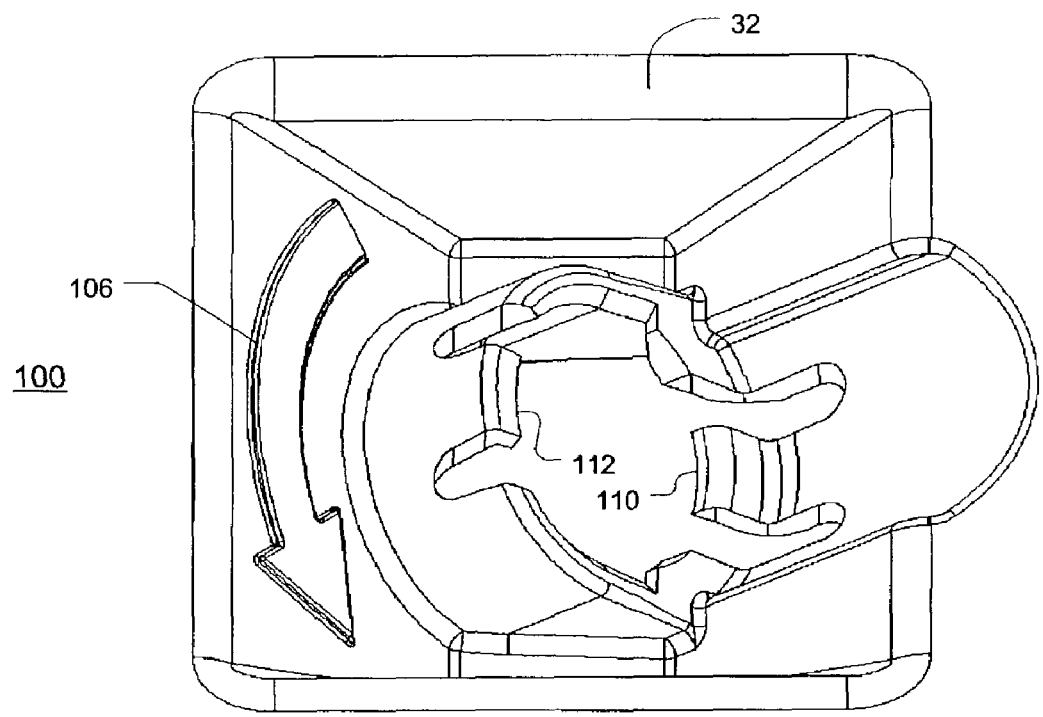
FIG. 2 illustrates a top perspective view of the port shown in FIG. 1.

As shown in FIG. 1 and FIG. 2, is port 100, includes at least one tang 110. Tang 110 is arranged such that insertion of a pen needle will allow tang 110 to engage the pen needle for removal of the pen needle from the pen syringe and deposit of the pen needle into sharps container 25. Also shown disposed on port 100 is optional top tang 112, which facilitates in the removal of the pen needle, however top tang 112 is not critical for the operation of the present invention. Top tang 112 functions to balance the forces exerted on the pen needle during removal, as top tang 112 is disposed substantially opposing tang 110 within port 100. Although top tang 112 is not critical to the functionality of the present invention, it does improve the operation of the present invention by virtue of balancing the forces during removal and not allowing a moment to be placed on the pen needle during removal. Optionally, either tang 110 or top tang 112 may be cantilevered such that upon insertion of a pen needle the tangs are free to move in a radial direction and allow for the easy insertion of the pen needle into port 100.

Figure 3:
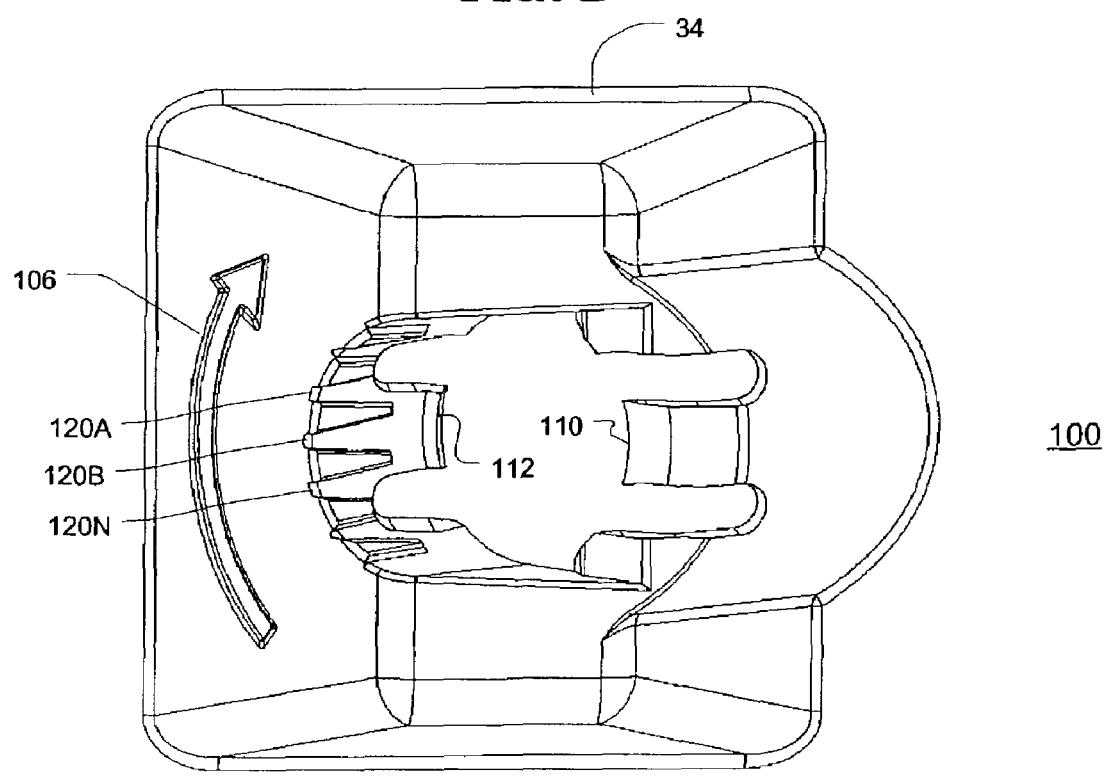
FIG. 3 illustrates a bottom perspective view of the port of FIG. 2.

FIG. 3 shows a bottom perspective view of port 100 and bottom surface 34 from the interior of sharps container 25. FIG. 3 also shows a plurality of teeth 120A, 120B, . . . 120N disposed in port 100. It is not critical to the invention to have a plurality of teeth, in that only one tooth is required for the functionality of the invention. Herein the terms tooth and teeth are used interchangeably. However, a plurality of teeth 120A, 120B, . . . 120N does improve the operation of the present invention by virtue of distributing the torque during removal of the pen needle. Teeth 120A, 120B, . . . 120N are disposed in an arcuate path about center axis 50 of port 100 (Shown in FIG. 6).

Figure 4:
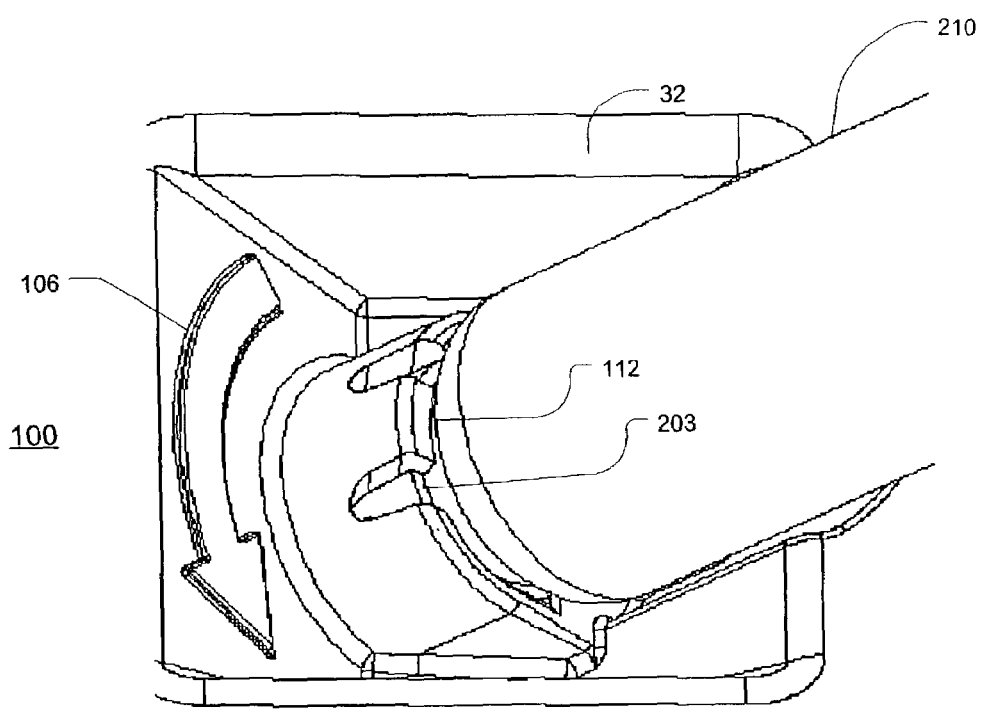
FIG. 4 illustrates a top perspective view of the port of FIG. 2, with a pen syringe inserted into the port.
Figure 5:
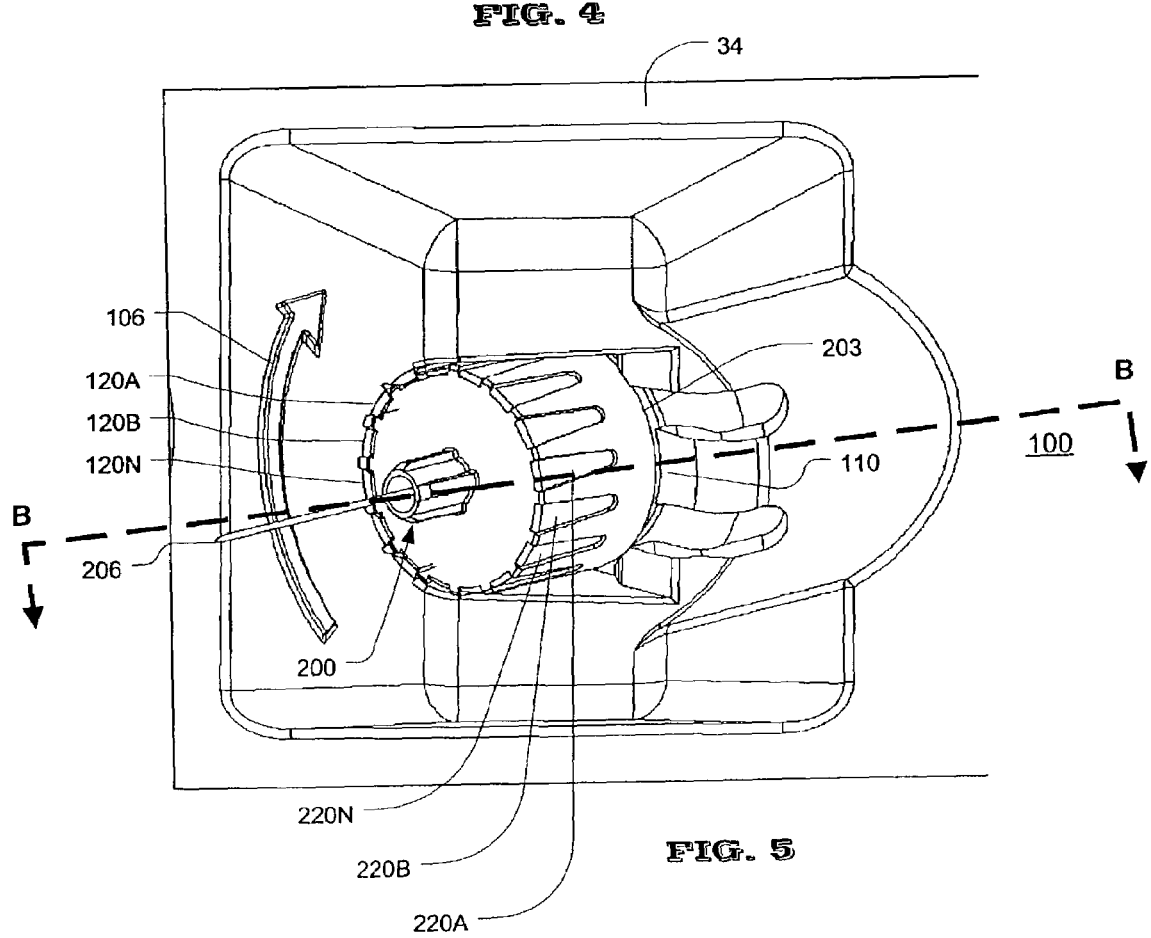
FIG. 5 illustrates a bottom perspective view of the port and pen syringe of FIG. 4.
Figure 6:
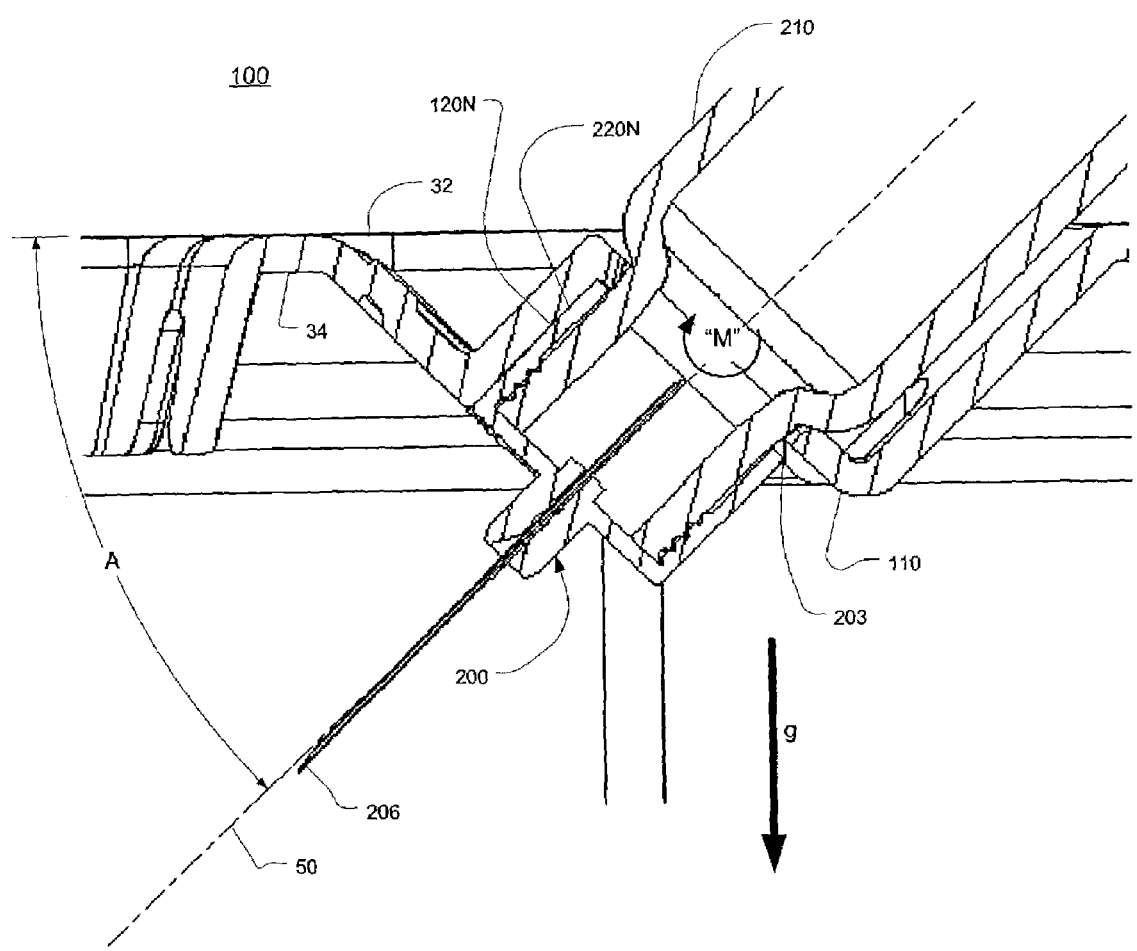
FIG. 6 illustrates a cross sectional view of the port and Pen Syringe of FIG. 4. along B—B.

Now referring to FIG. 4, FIG. 5 and FIG. 6, which show top and bottom perspective views, and a cross-sectional view, respectively, of port 100 in operation. During use, the patient inserts a distal tip 206 of needle 200 into port 100 along port axis 50. Teeth 120A, 120B, . . . 120N are configured such that they are a negative image of ribs 220A, 220B, . . . 220N on the pen needle so that the teeth may engage the ribs on the pen needle to prevent rotation of pen needle during removal of the pen needle from the pen syringe. Ribs 220A, 220B, . . . 220N are shown in FIG. 5, although only one rib is required for use of the invention; the term rib 220 or ribs 220 are used interchangeably. Although FIG. 5 shows a plurality of ribs 220 A through 220 N on needle 200, it is only essential that there be at least one rib to engage with at least one tooth to limit rotation of the pen needle about port axis 50. As needle 200 passes through port 100 teeth 120A . . . N in port 100 engage ribs 220A . . . N on needle 200. When needle 200 is entirely passed through port 100, proximal end 203 is past at least tang 110. At this point there is an audible click to indicate to the patient that pen needle 200 has been fully inserted into port 100. Tang 110 then limits proximal movement of needle 200 along axis 50. The patient then rotates pen syringe 210, which is threadably engaged to needle 200. Since rib(s) 220 are engaged to teeth 120, pen needle 200 is constrained from rotation relative to sharps container 25.

As the patient continues to rotate pen syringe 210, pen syringe 210 becomes disengaged from needle 200. When pen syringe 210 is fully disengaged from pen needle 200, the patient moves pen syringe 210 in a proximal direction, and since tang 110 is interfering with movement of needle 200 in the proximal direction, needle 200 remains within sharps container 25. Since in normal usage, the bottom 40 of sharps container 25 is placed a lower elevation than port 100 and top surface 32 is substantially parallel to the ground, gravitational forces then act on needle 200 to allow needle 200 to fall into sharps container 25 un-aided and without the use of a secondary operation. Thus, needle 200 is removed from pen syringe 210 with the use of port 100 containing critical features teeth 120 and tang 110.

As shown in FIG. 6, tang 110 and teeth 120 do not impede movement of pen needle 200 in the downward direction as indicated by the arrow labeled g. Port 100 is configured such that port axis 50 is at a substantial angle to top surface 32 which enables tang 110 and teeth 120 to be clear of interference of movement of pen needle 200 along axis 50 in the downward direction. FIG. 6 shows an exemplary angle, shown as "A," of axis 50 to top surface 32 at approximately 45 degrees. Angle "A' also allows the use of an arcuate pattern of teeth 120 which do not fully encircle pen needle 200 when pen needle 200 is inserted into port 100. In other designs, the teeth are in an arcuate path, fully encircling the pen needle. In the other designs, where the needle is fully encircled, the needle is not allowed to freely fall into the sharps container. Therefore, it is critical for the present invention to operate that teeth 120 do not fully encircle needle 200 in port 100. Use of an non-encircling pattern of teeth present a problem, however, in that at times during the attempted removal of needle 200 not all teeth 120 will be engaged to ribs 220 to prevent rotation of needle 200. This condition results in rotation of pen needle 200 relative to sharps container 25 and not relative to pen syringe 210. Therefore, engagement of teeth 120 to ribs 220 must therefore be ensured. By tilting axis 50 of port 100 relative to a gravity vector, the problem of ensuring engagement of teeth to ribs is resolved. The tilting of axis 50 at an exemplary angle "A" facilitates a moment "M" that the patient places on pen syringe 210 during rotation of pen syringe 210. Moment "M" is about an axis substantially perpendicular to axis 50. Moment "M" on pen syringe 210 ensures engagement of teeth 120 to ribs 220 while rotating pen syringe 210 about axis 50 for removal of pen needle 200 by forcing teeth 120 to engage ribs 220. Configuration of port 100 with a tilted axis 50 also improves the present invention by making the inadvertent removal of pen needles from sharps container 25 more difficult since top tang 112 interferes with pen needles trying to exit sharps container 25.

The invention has now been described in detail, however, it will be appreciated that certain changes and modifications may be made. For example, although illustrated in the context of disposing of pen needles, the apparatus and methods may be employed to dispose of other types of needles or sharps that may be threadably attached to other types of medical devices. Therefore, the scope and content of this invention are not limited by the foregoing description. Rather the scope and content are to be defined by the following claims:

We claim:

1. A closure for a sharps container for the disposal of a needle comprising:
   a. a top surface and a bottom surface wherein said bottom surface is on an interior of said sharps container;
   b. a passage located between said top surface and said bottom surface for the transfer of said needle into said sharps container;
   c. disposed within said passage is a plurality of teeth for partially encircling said needle, said teeth being disposed for engaging said needle to prevent rotation of said needle about a center axis of said passage and being disposed in an arcuate path about said center axis; and
   d. disposed within said passage is a tang, said tang being disposed for engaging said needle to prevent translation of said needle along said center axis, wherein said teeth and said tang do not impede the transfer of said needle into said sharps container by gravitational action.

2. The closure according to claim 1 wherein said center axis is at an angle substantially less than 90 degrees to said top surface.

3. The closure according to claim 1 wherein said tang is cantilevered.

4. The closure according to claim 1 wherein said plurality of teeth extend around said passage less than half of said passage's circumference.

5. The closure according to claim 1 wherein said closure has a handle.

6. The closure according to claim 1 wherein said closure contains an integrally molded lid.

7. The closure according to claim 1 wherein said passage includes indicia for advising a patient as to the proper removal of said needle.

8. The closure according to claim 1 further comprising a pair of tangs for engaging said needle to prevent translation of said needle along said center axis, wherein said pair tangs are disposed opposing each other within said passage.

9. The closure according to claim 8 wherein said pair of tangs are cantilevered.

10. A closure for a sharps container for the disposal of a needle comprising:
    a. a top surface and a bottom surface wherein said bottom surface is on an interior of said sharps container;
    b. a passage located between said top surface and said bottom surface for the transfer of said needle into said sharps container;
    c. disposed within said passage is a plurality of teeth for partially encircling said needle, said teeth being disposed for engaging said needle to prevent rotation of said needle about a center axis of said passage, wherein said center axis is at an angle substantially less than 90 degrees to said top surface and said teeth are disposed in an arcuate path about said center axis; and
    d. disposed within said passage is a pair of tangs, said pair of tangs being disposed for engaging said needle to prevent translation of said needle along said center axis, wherein said teeth and said tangs do not impede the transfer of said needle into said sharps container by gravitational action.

* * * * *